(12) United States Patent
Tsuchikawa et al.

(10) Patent No.: US 9,164,029 B2
(45) Date of Patent: Oct. 20, 2015

(54) METHOD OF CLASSIFYING AND DISCERNING WOODEN MATERIALS

(71) Applicants: Sumitomo Electric Industries, Ltd., Osaka-shi (JP); National University Corporation Nagoya University, Nagoya-shi (JP)

(72) Inventors: Satoru Tsuchikawa, Nagoya (JP); Hikaru Kobori, Nagoya (JP); Sakura Higa, Nagoya (JP)

(73) Assignees: Sumitomo Electric Industries, Ltd., Osaka-shi (JP); National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 14/367,199

(22) PCT Filed: Aug. 14, 2013

(86) PCT No.: PCT/JP2013/071926
§ 371 (c)(1),
(2) Date: Jun. 19, 2014

(87) PCT Pub. No.: WO2014/050339
PCT Pub. Date: Apr. 3, 2014

(65) Prior Publication Data
US 2014/0340670 A1  Nov. 20, 2014

(30) Foreign Application Priority Data

Sep. 25, 2012  (JP) .................... 2012-211157

(51) Int. Cl.
*G01N 21/55*  (2014.01)
*G01N 21/3563*  (2014.01)
(Continued)

(52) U.S. Cl.
CPC .......... *G01N 21/3563* (2013.01); *G01N 21/359* (2013.01); *G01N 33/46* (2013.01)

(58) Field of Classification Search
CPC ..... G01N 21/553; G01N 21/55; G01N 21/554; G01N 21/474; G01N 21/57
USPC ........................................................ 356/445
See application file for complete search history.

(56) References Cited

U.S. PATENT DOCUMENTS

2011/0317001 A1* 12/2011 Massen .................... 348/91

FOREIGN PATENT DOCUMENTS

JP  2000-502806 A  3/2000
JP  2002-005827 A  1/2002
(Continued)

OTHER PUBLICATIONS

H. Kobori et al., "Discriminant Analyzing System for Wood Wastes Using a Visible-Near-Infrared Chemometric Imaging Technique," Applied Spectroscopy, vol. 62, No. 8, (2008), pp. 854-859.
(Continued)

*Primary Examiner* — Tarifur Chowdhury
*Assistant Examiner* — MD Rahman
(74) *Attorney, Agent, or Firm* — Venable LLP; Michael A. Sartori; Trent B. Ostler

(57) ABSTRACT

A score of each of multiple pieces of reflection spectrum information included in a population is calculated using a first second principal component loading acquired by a principal component analysis, and a first group is classified based on the calculated score. Then, a score of each of multiple pieces of reflection spectrum information included in the population is calculated using a second second principal component loading acquired by a principal component analysis on a second population in which the reflection spectrum information of the first group is not included, and a second group is classified based on the calculated score. By performing a second principal component analysis using the second population, the second group can be accurately classified based on minute characteristics of each type of material included in the reflection spectrum information and the classification can be performed with a high accuracy.

2 Claims, 14 Drawing Sheets

(51) Int. Cl.
*G01N 21/359* (2014.01)
*G01N 33/46* (2006.01)

(56) References Cited

FOREIGN PATENT DOCUMENTS

| JP | 2002-090295 A | 3/2002 |
|----|---------------|--------|
| JP | 2007-278908 A | 10/2007 |
| JP | 2010-175528 A | 8/2010 |
| JP | 2011-017565 A | 1/2011 |
| JP | 2011017565 * | 1/2011 |

| WO | WO-2005/050176 A1 | 6/2005 |

OTHER PUBLICATIONS

H. Chen et al., "Qualitative and quantitative analysis of wood samples by Fourier transform infrared spectroscopy and multivariate analysis," Carbohydrate Polymers, 82, (2010), pp. 772-778.

International Search Report in PCT International Application No. PCT/JP2013/071926, dated Sep. 10, 2013.

International Preliminary Report on Patentability in PCT International Application No. PCT/JP2013/071926, mailed Mar. 31, 2015.

* cited by examiner

METHOD OF CLASSIFYING AND DISCERNING WOODEN MATERIALS

TECHNICAL FIELD

The present invention relates to a method of classifying and discerning wooden materials.

BACKGROUND ART

So-called engineering woods, such as preserved woods, plywood, overlaid panels, and the like, are difficult to be reused without change, and are often treated as industrial waste. For the effective use of wooden resources, it is necessary to classify wooden materials based on whether the wooden materials can be reused or not, the types of wooden materials, and the like.

CITATION LIST

Patent Literature

Patent Literature 1: Japanese Unexamined Patent Application Publication No. 2007-278908

Non Patent Literature

Non Patent Literature 1: Hikaru Kobori et al., Applied spectroscopy, 62(8), 854-859, 2008

SUMMARY OF INVENTION

Technical Problem

However, if wooden materials are determined one by one by visual inspection, etc., the processing time is lengthened, resulting in an inefficient processing. Further, in order to enable a wooden material to be reused even after the classification thereof, it is necessary to sufficiently raise the classification accuracy.

The present invention has been made in view of the above-mentioned matters, and an object of the prevent disclosure is to provide a method of accurately and efficiently classifying and discerning wooden materials.

Solution to Problem

In order to achieve the object described above, a method of classifying wooden materials according to an embodiment of the present invention includes the steps of: acquiring a first second principal component loading by performing a principal component analysis on a population including multiple pieces of reflection spectrum information obtained by measuring a plurality of different wooden materials; calculating a score of the first second principal component loading for each of the multiple pieces of reflection spectrum information included in the population; classifying into a first group from the population a wooden material having reflection spectrum information having the score belonging to a predetermined range; acquiring a second second principal component loading by performing a principal component analysis on a second population obtained by removing the reflection spectrum information belonging to the first group from the population; calculating a second score of the second second principal component loading for each of multiple pieces of reflection spectrum information included in the second population; and classifying into a second group from the second population a wooden material having reflection spectrum information, the second score of which belongs to a predetermined range.

According to the method of classifying wooden materials described above, scores of multiple pieces of reflection spectrum information included in the population are calculated using the first second principal component loading acquired by a principal component analysis, and the first group is classified based on the calculated scores. Then, the scores of the multiple pieces of reflection spectrum information included the population are calculated using the second second principal component loading acquired by the principal component analysis for the second population in which the reflection spectrum information of the first group is not included, and the second group is classified based on the calculated scores. In this event, by performing a second principal component analysis using a second population obtained by removing reflection spectrum information of the first group from the population, it is possible to accurately classify the second group based on minute characteristics of each kind of material included in the reflection spectrum information and it is possible to achieve a classification with high accuracy. Further, because classification of wooden materials can be performed by acquiring reflection spectrum information of the wooden materials, it is possible to achieve a more efficient classification than the conventional classification.

In addition, a method of method of discerning wooden materials comprising: calculating a first unknown score of the unknown reflection spectrum information by using a first second principal component loading obtained by performing a principal component analysis on a population including multiple pieces of reflection spectrum information obtained by measuring a plurality of different wooden materials, the an unknown reflection spectrum information obtained by measuring an unknown wooden material; discerning that a wooden material having the unknown reflection spectrum information belongs to a first group when the first unknown score is included in a range of scores of the first second principal component loading, the scores classifying the different wooden materials into the first group from the population; calculating, when the wooden material having the unknown reflection spectrum information is discerned that it does not belong to the first group, a score of the first second principal component loading for each of the multiple pieces of reflection spectrum information included in the population, classifying into a first group from the population a wooden material having the score of which is included in a predetermined range, and then calculating a second unknown score of the unknown reflection spectrum information by using a second second principal component loading obtained by performing a principal component analysis on a second population obtained by removing the reflection spectrum information belonging to the first group from the population; and discerning that a wooden material having the unknown reflection spectrum information belongs to a second group when the second unknown score is included in a range of scores of the second second principal component loading, the scores classifying the different wooden materials into the second group from the second population.

According to the method of discerning wooden materials as described above, a score of the unknown reflection spectrum information of an unknown material is calculated based on the first second principal component loading, and it is then determined whether a wooden material belongs to the first group by discerning whether the calculated score is included in a range classifying the first group. Further, when the wooden material does not belong to the first group, a score based on the second second principal component loading is calculated, and it is then determined whether the wooden material belongs to the second group by discerning whether the calculated score is included in the range classifying the second group. In this manner, a classification of an unknown material is determined using a single piece of unknown reflection spectrum information. Further, the classification using a score based on a first second principal component loading and a score based on a second second principal component loading can be performed with a high accuracy. Therefore, a group to which a wooden material belongs can be determined more conveniently and with a higher accuracy.

Advantageous Effects of Invention

According to the present invention, a method of accurately and efficiently classifying and discerning wooden materials is provided.

DESCRIPTION OF EMBODIMENTS

Figure 1:
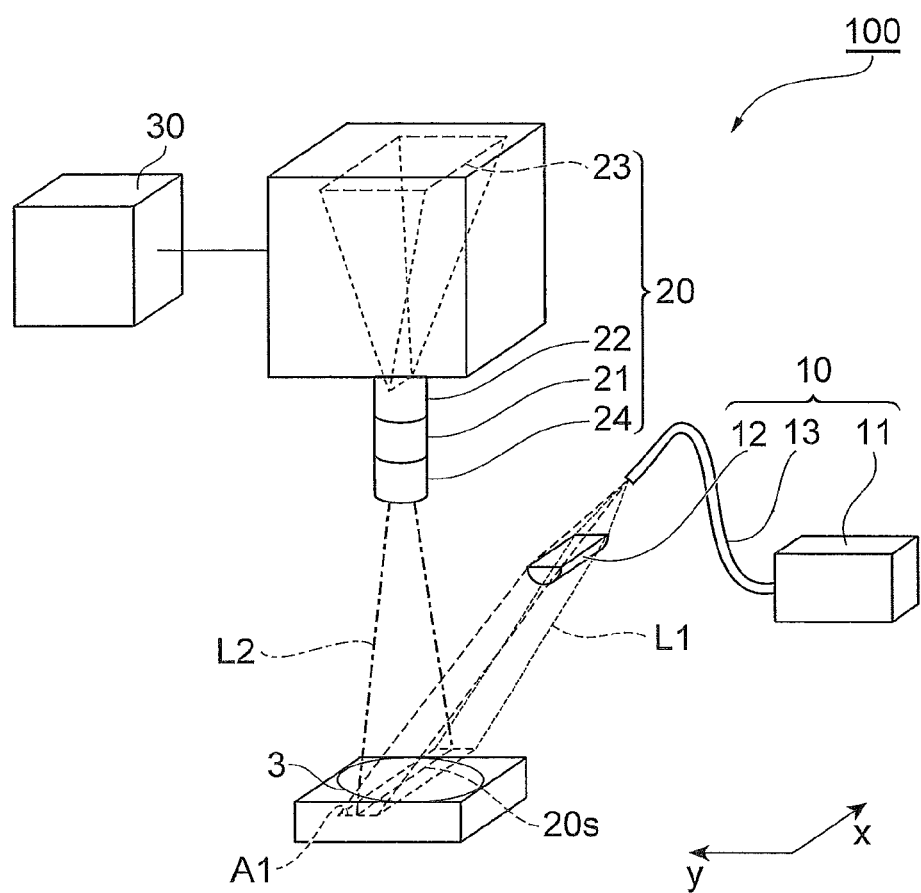
FIG. 1 is a diagram for describing the configuration of a measurement system according to an embodiment of the present invention.

Hereafter, embodiments of the present invention will be described in detail with reference to the accompanying drawings. In addition, in the description of the drawings, the same reference numerals are given to the same elements and repeated description thereof is omitted.

(Configuration of a Wooden Material Measurement System)

A measurement system 100 according to the present embodiment will be described with reference to FIG. 1. The measurement system 100 according to the present embodiment is a device for detecting alien materials mixed in a measuring object 3. A wooden material may be used as the measuring object 3 of the measurement system 100 according to the present embodiment. A wooden material is a material obtained by decomposing a raw wooden material into elements and then reconstituting the elements. Also, the wooden material may have been subjected to additional processes of preservative treatment, coating and the like.

The measurement system 100 is a device for measuring a spectrum of a diffusion reflection light obtained by irradiating a measurement light onto the measuring object 3. The measurement system 100 includes an irradiation means 10, an imaging means 20, and an analysis means 30.

The irradiation means 10 irradiates a measurement light having a constant wavelength band toward a predetermined irradiation region A1. The wavelength range of the measurement light irradiated by the irradiation means 10 is appropriately selected according to the measuring object 3. A near-infrared light including a part or all of a light having a wavelength in a wavelength range from 1000 nm to 2500 nm may be suitably used, and a plurality of lights having different wavelengths within the wavelength range are used for measurement. Further, the irradiation means 10 including a halogen lamp 11 is described in the present embodiment.

The irradiation region A1 is a region corresponding to a part of the surface of the measuring object 3. The irradiation region A1 is an area extending in a shape of a widened line in the x axis direction of FIG. 1. Further, the width of the irradiation area A1 in a direction (y axis direction of FIG. 1) perpendicular to the extending direction of the irradiation region A1 is 10 mm or less.

The irradiation means 10 includes a halogen lamp 11, an irradiation unit 12, and a bundle optical fiber 13 that interconnects the halogen lamp 11 and the irradiation unit 12. The halogen lamp 11 generates a broad band light including a near-infrared light.

The bundle optical fiber 13 includes light guides (for example, 1500 light guides), and the light guides are bundled in a circular shape at one end of the bundle optical fiber and are arranged to form a rectangular cross section (for example, 3×500 matrixes) at the other end thereof. The near-infrared light generated by the halogen lamp 11 is incident to the circularly bundled end surface of the bundle optical fiber 13 and is emitted from the other end surface face at which the light guides are arranged in a rectangular shape. The use of the bundle optical fiber 13 enables an efficient realization of a light source of a line shape.

The irradiation unit 12 irradiates the near-infrared light emitted from the end surface of the bundle optical fiber 13 to the irradiation region A1 at which the measuring object 3 is placed. Since the irradiation unit 12 receives the near-infrared light emitted from the bundle optical fiber 13 and then emits the near-infrared light in a one-dimensional line shape corresponding to the irradiation region A1, a cylindrical lens is properly used as the irradiation unit 12. In this way, the near-infrared light L1 formed in a line shape in the irradiation unit 12 is irradiated onto the irradiation region A1 from the irradiation unit 12.

The near-infrared light L1 output from the irradiation means 10 is diffused and reflected by the measuring object 3 placed at the irradiation region A1. Further, a part of the diffused and reflected near-infrared light is incident to the imaging means 20 as a diffusion reflection light L2.

Figure 2:
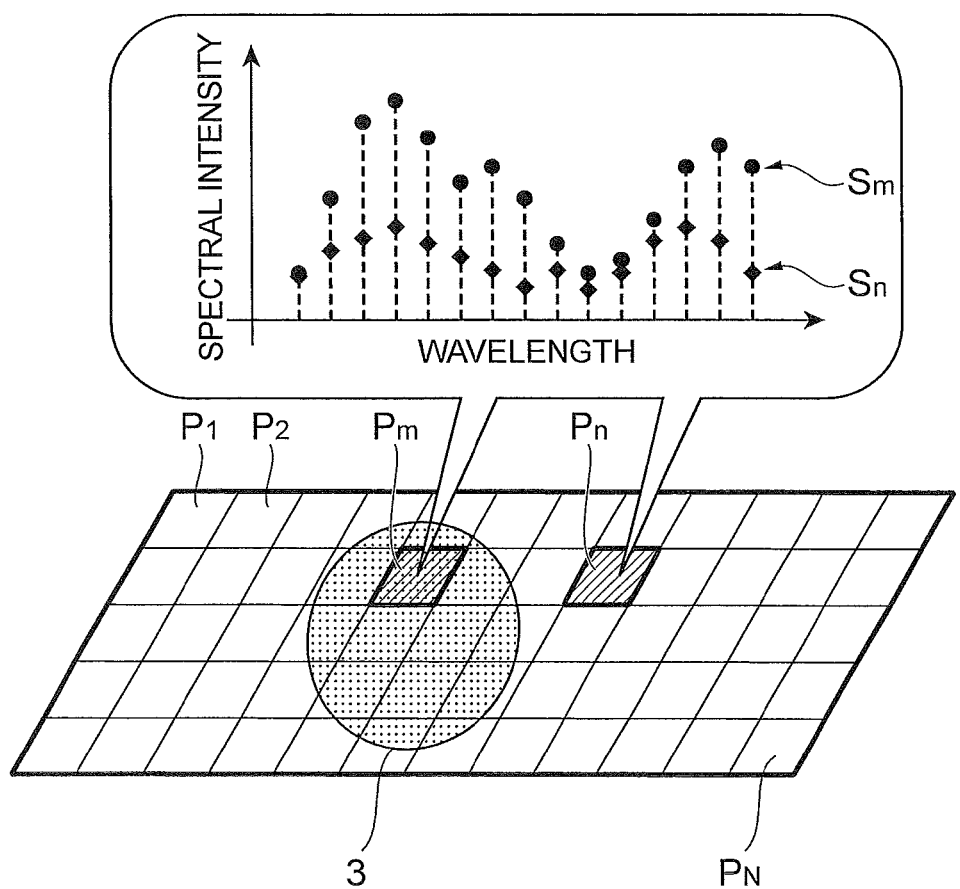
FIG. 2 is a diagram for describing a hyper spectral image.

The imaging means 20 has a function as a hyperspectral sensor for acquiring a hyperspectral image. Now, the hyperspectral image in the present embodiment will be described using FIG. 2. FIG. 2 is a diagram schematically explaining a hyperspectral image. As shown in FIG. 2, a hyperspectral image is an image configured by N number of pixels $P_1 \sim P_N$. FIG. 2 specifically shows two pixels $P_m$ and $P_n$ as an example of the N number of pixels. The pixels $P_m$ and $P_n$ include spectrum information $S_m$ and $S_n$, each of which includes a plurality of intensity data, respectively. The intensity data is data showing the spectral intensity at a particular wavelength (or wavelength band). FIG. 2 shows 15 pieces of intensity data possessed as spectrum information $S_m$ and $S_n$ in a state where they are superposed. Due to the characteristic that each pixel constituting the image has multiple pieces of intensity data, the hyperspectral image H corresponds to data with a three-dimensional configuration, which has both a two-dimensional element as an image and an element as spectral data. Further, in the present embodiment, the hyperspectral image H refers to an image configured by pixels, each of which has intensity data in at least five wavelength bands. In addition, the measuring object 3 is also shown in FIG. 2. That is, in FIG. 2, $P_m$ is a pixel obtained by imaging the measuring object 3 and $P_m$ is a pixel obtained by imaging the background (For example, the mounting table of the measuring object 3).

Referring back to FIG. 1, the imaging means 20 according to the present embodiment includes a camera lens 24, a slit 21, a spectroscope 22, and a light receiving unit 23. In the imaging means 20, the viewing area 20s s is an area having a line shape, which extends in the same direction (x axis direction) as that of the irradiation region A1 and is included in the irradiation region A1, and the diffusion reflection light L2 having passed through the slit 21 forms an image of the viewing area 20s on the light receiving unit 23.

The slit 21 is provided with an opening formed in a direction parallel to the extending direction (x axis direction) of the irradiation region A1. The diffusion reflection light L2 having entered the slit 21 of the imaging means 20 is incident to the spectroscope 22.

The spectroscope 22 disperses the diffusion reflection light L2 in the longitudinal direction of the slit 21, that is, in a direction (y axis direction) perpendicular to the extending direction of the irradiation region A1. The light dispersed by the spectroscope 22 is received by the light receiving unit 23.

The light receiving unit 23 includes a light receiving surface on which a plurality of light receiving elements are two-dimensionally arranged, and each of the light receiving elements receives the light. As a result, the light receiving unit 23 receives lights according to the wavelengths of the diffusion reflection light L2, which have been reflected at positions along the width direction of the belt conveyor 2, respectively. Each of the light receiving elements outputs a signal according to the intensity of the received light as information relating to one point having a shape of a two dimensional plane, which is configured by a position and a wavelength. The signal output from the light receiving element of the light receiving unit 23 is sent, as image data relating to the hyperspectral image, from the imaging means 20 to the analysis means 30.

The analysis means 30 obtains a reflection spectrum (reflection spectrum information) of the diffusion reflection light L2 from the input signal and performs an inspection based on the obtained spectrum. Further, a result of the analysis by the analysis means 30 is output to, for example, a monitor, a printer, etc. which are connected to the analysis means 30, so that the result is notified to the operator of the measurement system 100.

The analysis means 30 includes a Central Processing Unit (CPU), a Random Access Memory (RAM) and a Read Only Memory (ROM) that are main memories, a communication module, such as such as an imaging means, which communicates with another device, and a computer equipped with hardware including an auxiliary memory device, such as a hard disk, etc.

(The Method of Classifying Wooden Materials)

Figure 3:
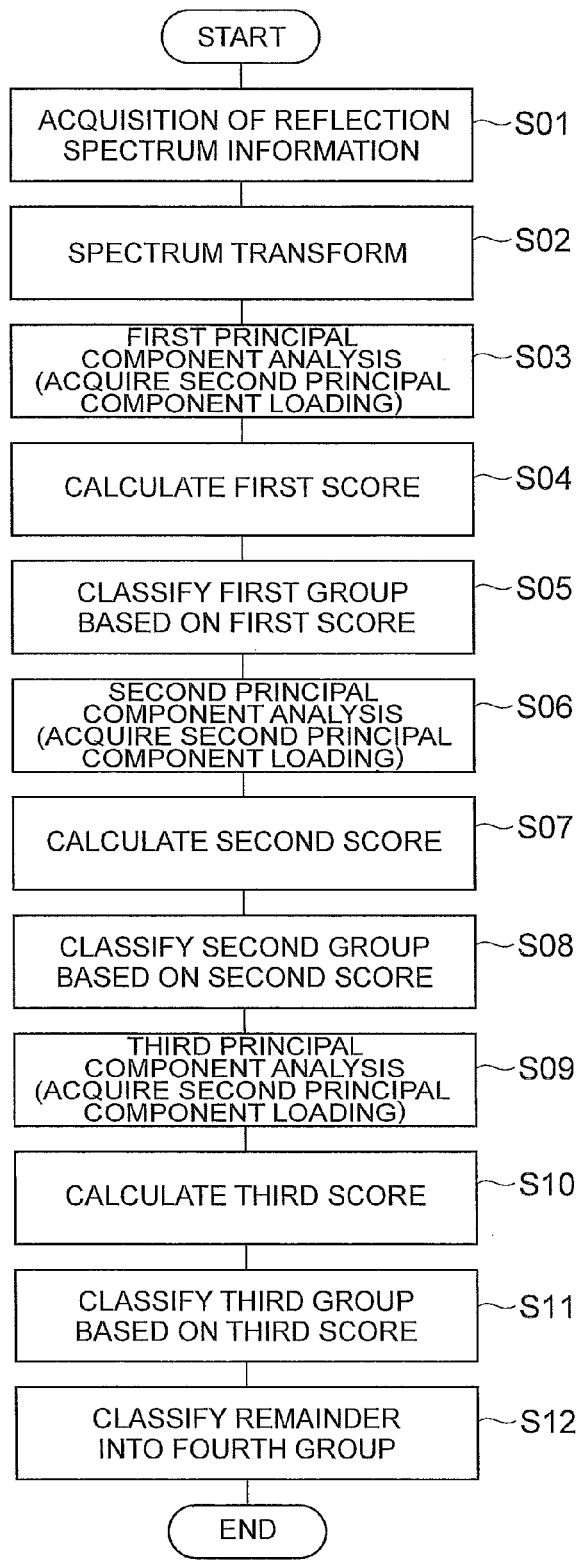
FIG. 3 is a diagram for describing a method of classifying wooden materials.

Next, a method of classifying wooden materials by using a hyperspectral image imaged by the measurement system 100 will be described. First, referring to FIG. 3, a method of classifying wooden materials by using reflection spectrum information of a plurality of wooden materials different from each other will be described. In the classification of the present embodiment, reflection spectrum information acquired from a plurality of known wooden materials is used to determine which material an unknown wooden material corresponds to, based on reflection spectrum information of the unknown wooden material. Further, the following description discusses a case in which a plurality of wooden materials to be measured is classified into four groups.

First, reflection spectrum information of a plurality of wooden materials different from each other are acquired (S01). Here, let us assume that each of the types of the wooden materials, reflection spectrum information of which is acquired, is already known. The types of wooden materials, which can be taken into consideration, include, for example, types based on the classification of wood, such as a broadleaved tree and a needle-leaved tree, and types based on the processing of the materials, such as preservative treatment-completed wood and painting-completed wood.

Next, a spectral transform of this reflection spectrum information is performed (S02). In the present embodiment, a differential processing as a spectral transform, especially a Savitzky-Golay second-order differential processing, is performed. As a result, the influence of a baseline or a drift can be excluded and the peak fluctuation of the reflection spectrum can be emphasized.

Thereafter, a first Principal Component Analysis (PCA) is performed using reflection spectrum information after the spectrum transform to acquire a second principal component loading (a first second principal component loading) (S03).

The principal component analysis is a technique of analysis used when there is data described by many variables, wherein the analysis is performed based on several uncorrelated comprehensive indicators abbreviated from the data while eliminating the correlation between the variables and minimizing the loss of information content. As used herein, the comprehensive indicators are called a first principal component, a second principal component, . . . , respectively. Here, the principal component can be linearly combined with each of the variables. Therefore, for the interpretation, it is effective to specify a variable having a strong influence on the principal component by understanding a correlation between the principal component and each variable. In this event, an indicator called loading (factor loading) is defined as a correlation coefficient between a principal component and a variable. That is, a second principal component loading is a correlation coefficient between the second principal component and each variable. The calculation of the second principal component loading may be performed by a method known to the public.

Next, a first score, which is a score of each wooden material, is calculated based on the first second principal component loading and reflection spectrum information after a spectrum transform relating to a population (S04). The calculation of the score may also be performed by a method known to the public.

Subsequently, a first group is classified from the population, based on the first score (S05). As a result of the calculation of the first score, it is possible to consider a case in which a particular type of wooden material shows a higher score than that of other types of wooden materials. Therefore, a material having a first score included in a pre-determined range (for example, a score higher than a threshold) is classified from the other materials and is determined as the first group. Further, in this step, when the type of the measured wooden material is already known and it is desired to classify a particular type of wooden material as the first group, it is also possible to determine the range of the score for the classification (determine a threshold) based on the variation of the first score, etc. In addition, the wooden material having been classified as the first group is removed from the population, and the remaining reflection spectrum information group after the spectrum transform is newly considered as a second population.

Next, a second principal component analysis is performed for the second population to acquire a second principal component loading (a second second principal component loading) (S06). The difference between the first principal component analysis and the second principal component analysis is that they use different populations as targets for the analysis.

Subsequently, a second score, which is a score of each wooden material, is calculated based on the second second principal component loading and reflection spectrum information after spectrum transform relating to the population (S07). Further, a second group is classified from the second population based on the second score (S08). The method in these steps is the same as that in the first round (S04, SO5). In addition, the wooden material classified as the second group is removed from the second population, and the reflection spectrum information group remaining in the second population is newly considered as a third population.

Further, in the same manner as described above, a third principal component analysis is performed for the third population to acquire a second principal component loading (a third second principal component loading) (S09), a third score, which is a score of each wooden material, is calculated based on the third second principal component loading and the reflection spectrum information after the spectrum transform relating to the population (S10), and a third group is then classified from the third population based on the third score (S11). The method in these steps is the same as that in the first round (S03 to S05) and the second round (S06 to S08). Further, the wooden material classified as the third group is removed from the third population. When the population is classified into the four groups as in the present embodiment, the wooden materials included in the third population after the third group is removed are considered as a fourth group (S12).

Through the above-mentioned process, the classification of the wooden materials is finished. In addition, the first second principal component loading, the range of the score for classifying the first group, the second second principal component loading, the range of the score for classifying the second group, the third second principal component loading, and the range of the score for classifying the third group, which are used the classification method described above, are also used in discerning a classification of an unknown wooden material as described below.

(Method of Discerning a Wooden Material)

Figure 4:
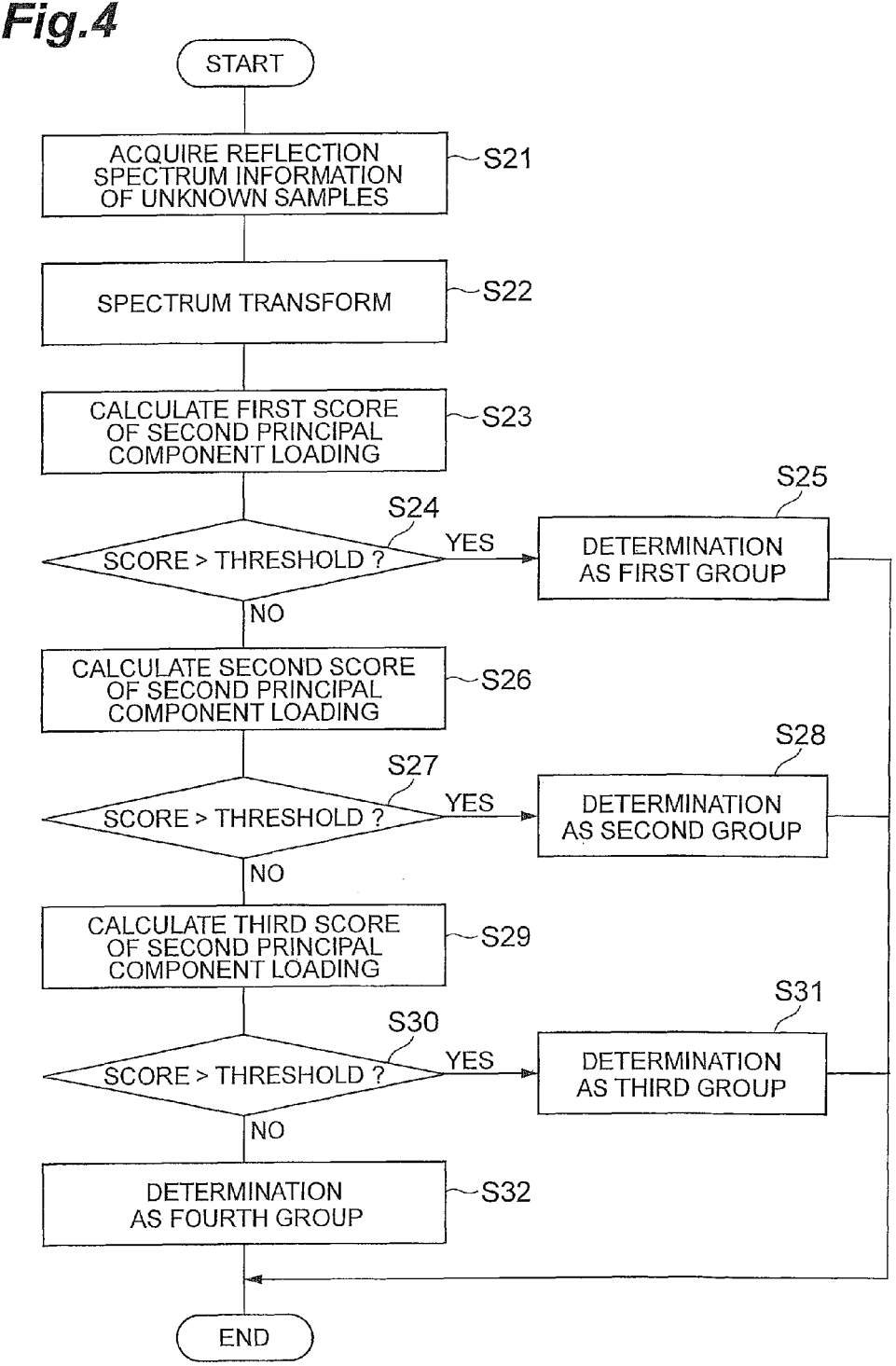
FIG. 4 is a diagram for describing a method of discerning wooden materials.

Subsequently, a method of discerning which group an unknown wooden material belongs to among the first to fourth groups classified as described above will be described with reference to FIG. 4.

First, a reflection spectrum (unknown reflection spectrum information) relating to an unknown wooden material is acquired using the measurement system 100 shown in the FIG. 1 (S21). In this event, the measured wavelength of the reflection spectrum is the same as that in the case where the classification of wooden materials is performed.

Next, a spectrum transform of the unknown reflection spectrum information is performed (S22). In the present embodiment, a differential processing, especially a Savitzky-Golay second-order differential processing, is performed as the spectrum transform.

Next, a first unknown score of the unknown reflection spectrum information is calculated based on the unknown reflection spectrum information after the spectrum transform and the first second principal component loading obtained at the time of classification of wooden materials (S23). Further, it is determined whether the obtained first unknown score belongs to a score range for the classification of the first group of wooden materials (for example, whether the obtained first unknown score is higher than a predetermined threshold) (S24). Here, if the obtained first unknown score belongs to the score range for the classification of the first group of wooden materials, it is determined that the wooden material belongs to the first group (S25). In contrast, if the obtained first unknown score does not belong to the score range for the classification of the first group of wooden materials, it is determined that the wooden material does not belong to the first group, and the next step is performed.

Next, it is determined whether the wooden material belongs to a second group. First, a second unknown score of the unknown reflection spectrum information is calculated based on the unknown reflection spectrum information after the spectrum transform and the second second principal component loading obtained in the classification of wooden materials (S26). Subsequently, it is determined whether the obtained second unknown score belongs to the score range for the classification of the second group (for example, whether the obtained second unknown score is higher than a predetermined threshold) (S27). If the second unknown score belongs to the score range for the classification of the second group, it is determined that the wooden material belongs to the second group (S28). In contrast, if the second unknown score does not belong to the score range for the classification of the second group, it is determined that the wooden material does not belong to the second group, and the next step is performed.

Further, in the same manner as described above, it is determined whether the wooden material belongs to the third group. That is, a third unknown score of the unknown reflection spectrum information is calculated based on the third second principal component loading obtained in the classification of wooden materials (S29). Subsequently, it is determined whether the obtained third unknown score belongs to the score range for the classification of the third group (for example, whether the obtained third unknown score is higher than a predetermined threshold) (S30). Here, if the third unknown score belongs to the score range for the classification of the third group, it is determined that the wooden material belongs to the third group (S31). In contrast, if the third unknown score does not belong to the score range for the classification of the third group, it is determined that the wooden material does not belong to any of the first to third groups and belongs to the fourth group (S32). Through the method described above, the type of the unknown wooden material can be determined.

Hereinafter, an embodiment of the classification of wooden materials into a plurality of groups through multiple times of principal component analysis as described above will be described.

First, multiple kinds of wooden materials were prepared. The kinds of wooden materials include a needle-leaved tree, a broad-leaved tree, a resin film overlay (a material having a resin film attached to one principal main surface thereof), and a preservative treated material.

Figure 5:
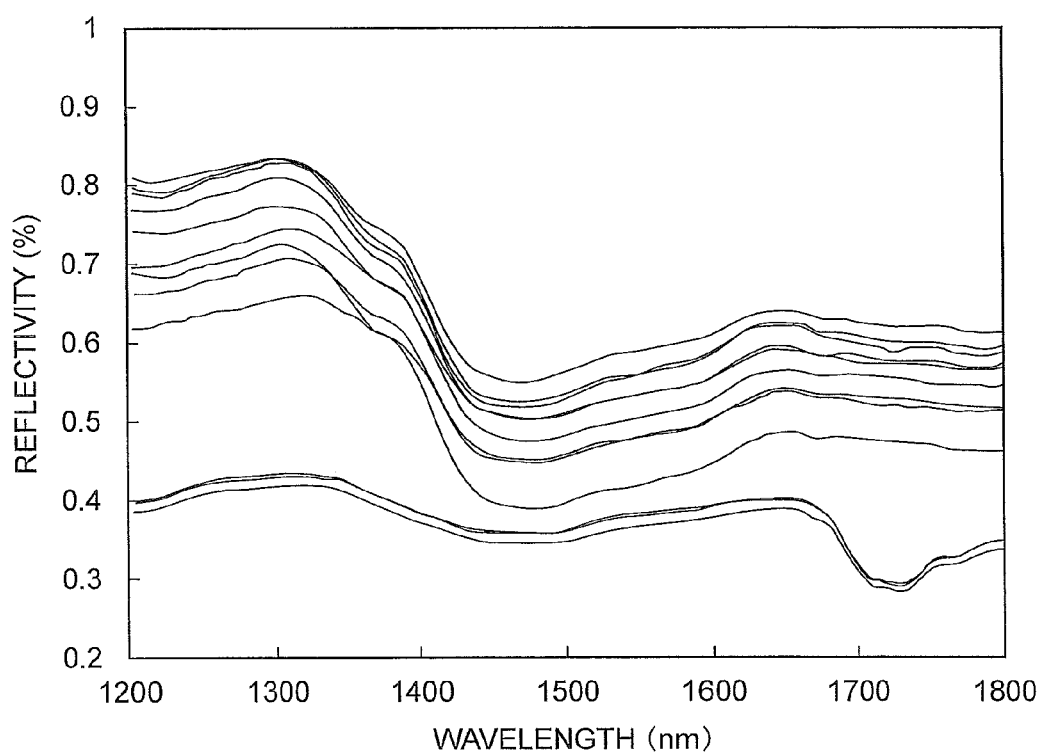
FIG. 5 is a diagram illustrating the reflection spectrum information of the population.

Three samples of each of these wooden materials were prepared, and reflection spectrums of the samples were measured in a wavelength range from 1000 nm to 2500 nm by using a measurement device (a composition imaging system named Compovision™: manufactured by Sumitomo Electric Industries Co., Ltd.) having a function equivalent to that of the measurement system 100 shown in FIG. 1. Regions obtained by imaging wooden materials are extracted from hyperspectral images obtained from results of the measurement and are then averaged to obtain an average reflection spectrum of the wooden materials. Further, a measurement wavelength interval was 6 nm and a spatial resolution was 312.5 μm. FIG. 5 shows only the wavelength range from 1200 nm to 1800 nm, and data of the wavelength range from 1200 nm to 1800 nm was used in the processing described below also.

Figure 6:
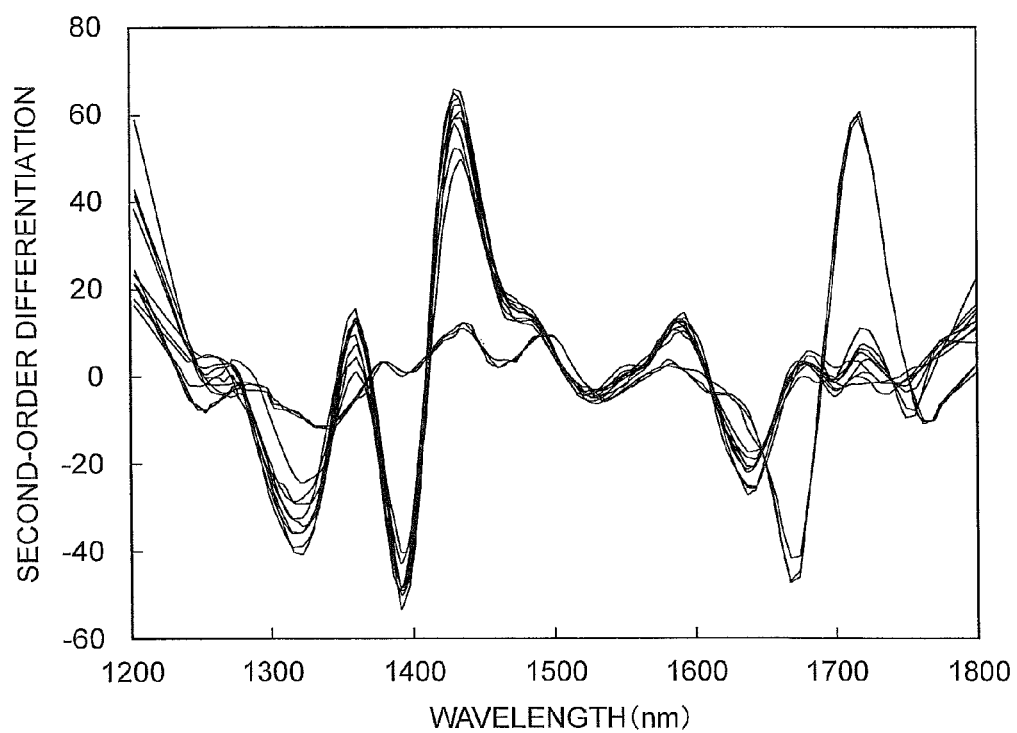
FIG. 6 is a diagram illustrating a result of a second-order differentiation of reflection spectral information of a population.
Figure 7:
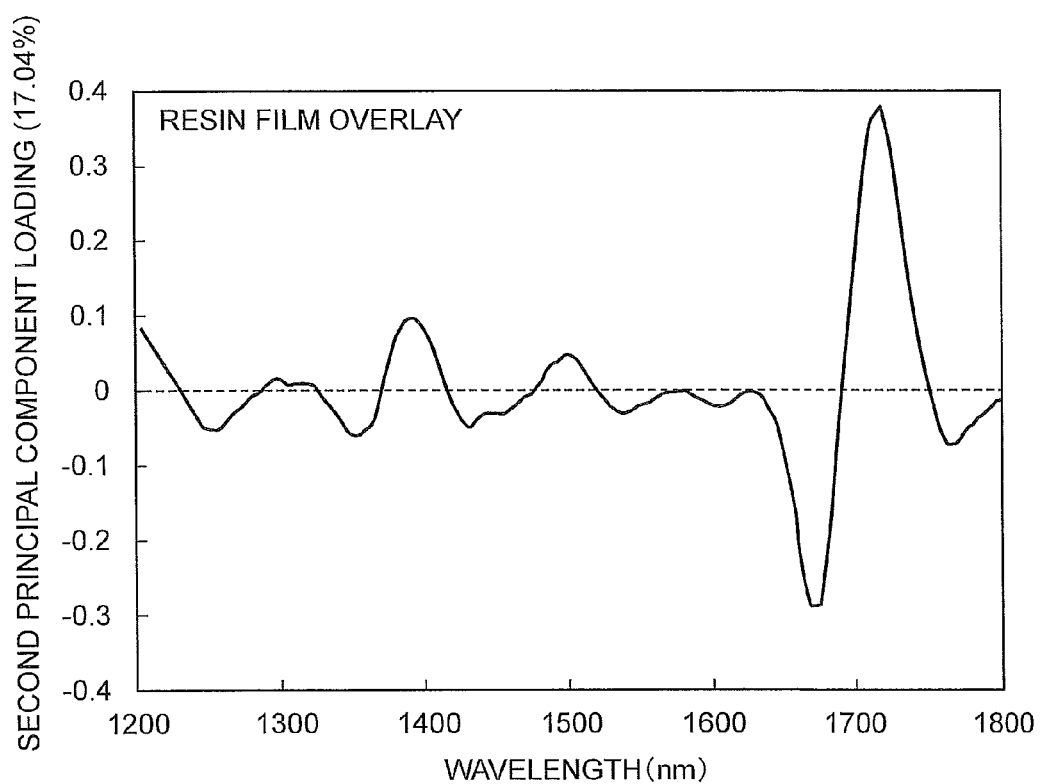
FIG. 7 is a diagram illustrating a first second principal component loading.
Figure 8:
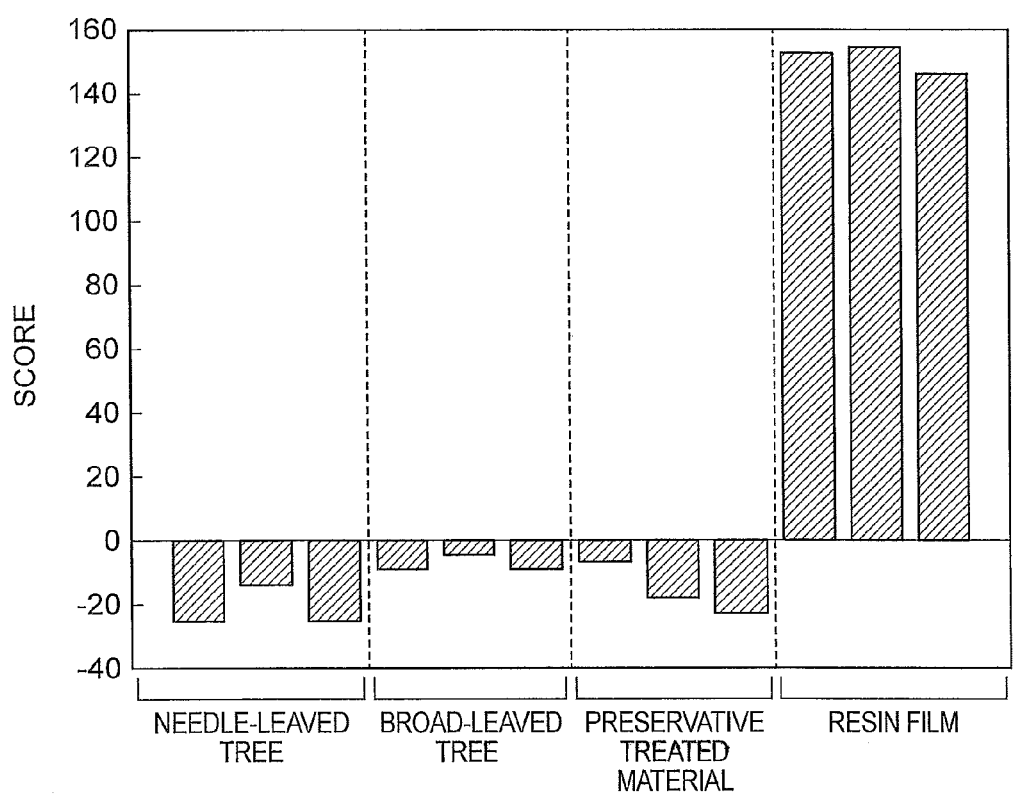
FIG. 8 is a diagram illustrating a result of calculation of scores for the first second principal component loading.

Next, a Savitzky-Golay second-order differential processing was performed for each reflection spectrum of FIG. 5. A result thereof is shown in FIG. 6. Further, a first second principal component loading of a resin film overlay obtained through a first principal component analysis using 12 samples as a population is shown in FIG. 7. Further, scores of 12 samples calculated using a first second principal component loading are shown in FIG. 8. FIG. 8 also shows which wooden material each of 12 samples is made of. As a result, it was noted that only 3 samples of a resin film overlay had higher scores than scores of samples of the other wooden materials. Therefore, the 3 samples of the resin film overlay can be classified into a first group by setting a threshold to, for example 0, and classifying samples satisfying a condition that score >0 into the first group.

Figure 9:
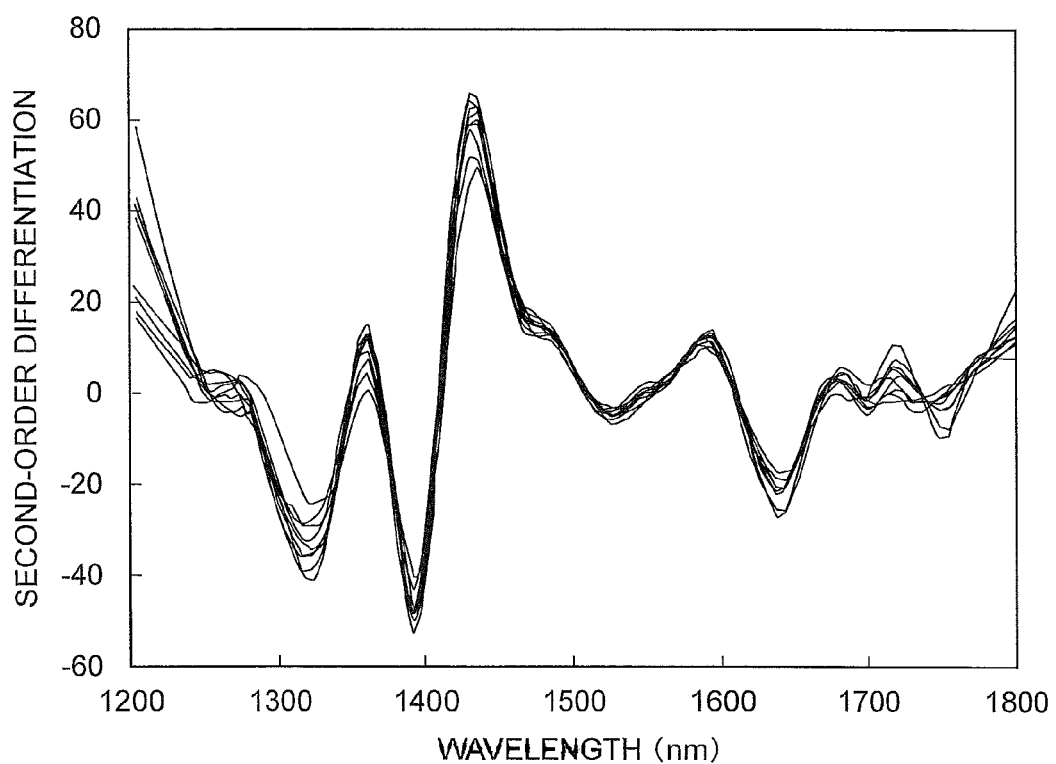
FIG. 9 is a diagram illustrating a result of a second-order differentiation of reflection spectrum information of a second population.
Figure 10:
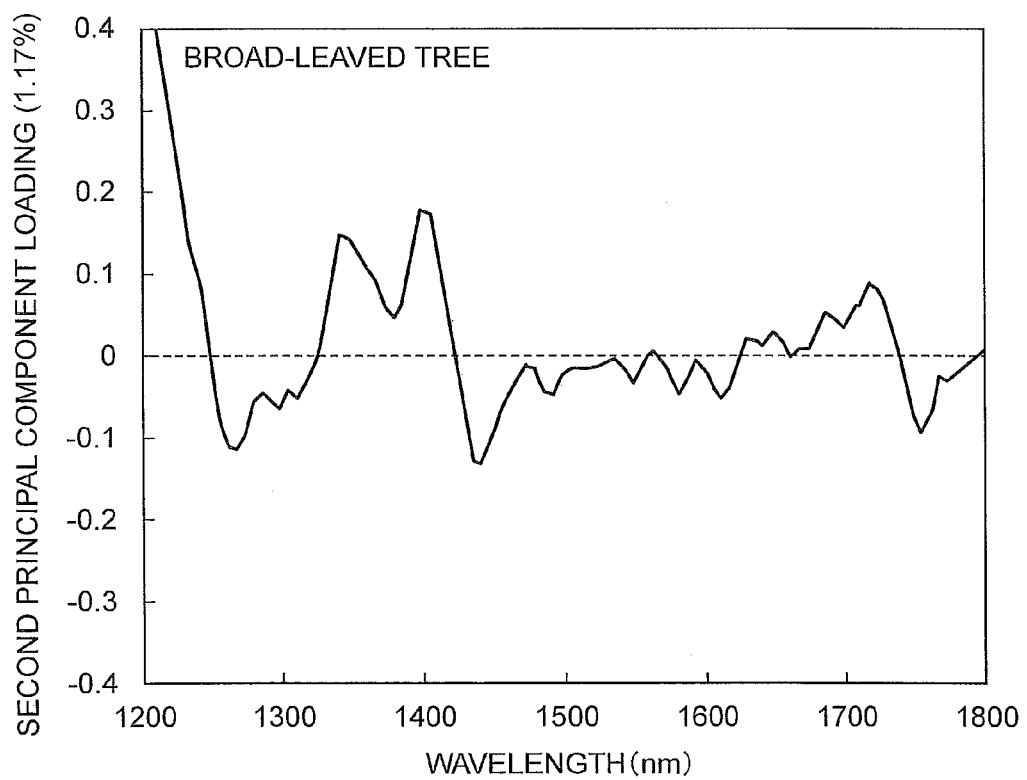
FIG. 10 is a diagram illustrating a second second principal component loading.
Figure 11:
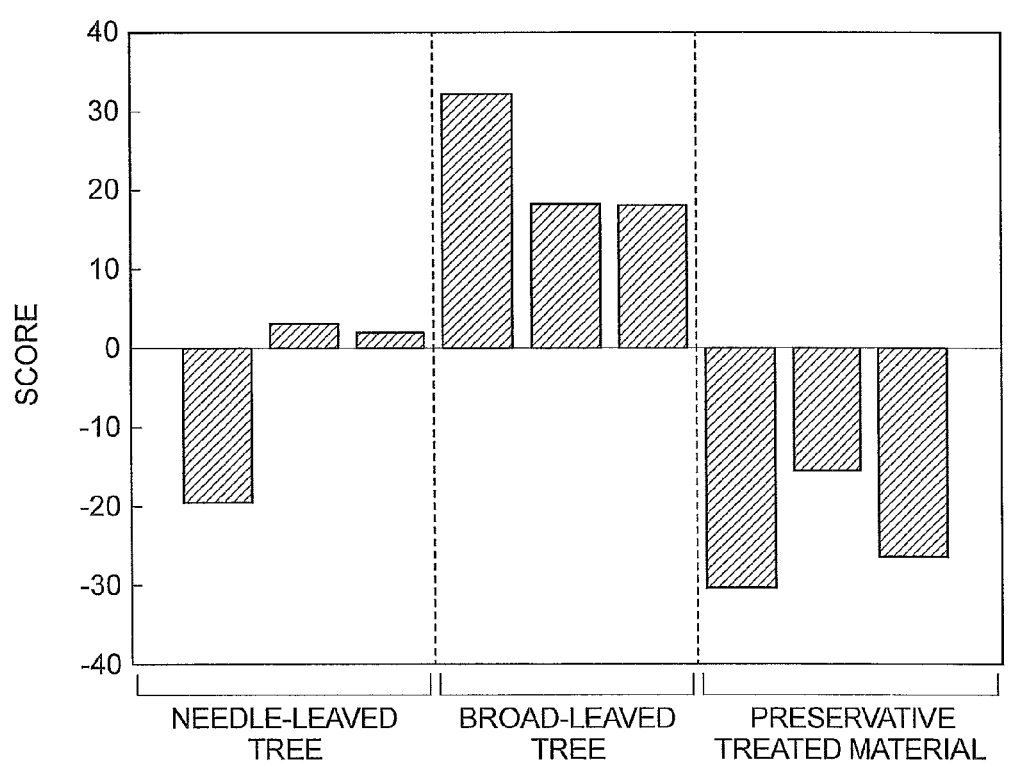
FIG. 11 is a diagram illustrating a result of calculation of scores for a second second principal component loading.

Next, classification of a second group is performed using 9 samples which constitute a second population remaining after removing the 3 samples classified into the first group from the population. First, results of second-order differential processing of the 9 samples of the second population are shown in FIG. 9. Further, a second second principal component loading of a broad-leaved tree acquired by performing a second principal component analysis on the second population is shown in FIG. 10. Further, scores of the 9 samples calculated using the second second principal component loading are shown in FIG. 11. As a result, it was noted that only 3 samples of the broad-leaved tree had higher scores than scores of the samples of the other wooden materials. Therefore, the 3 samples of the broad-leaved tree can be classified into a second group by setting a threshold to, for example 10, and classifying the samples satisfying a condition that score >10 into the second group.

Figure 12:
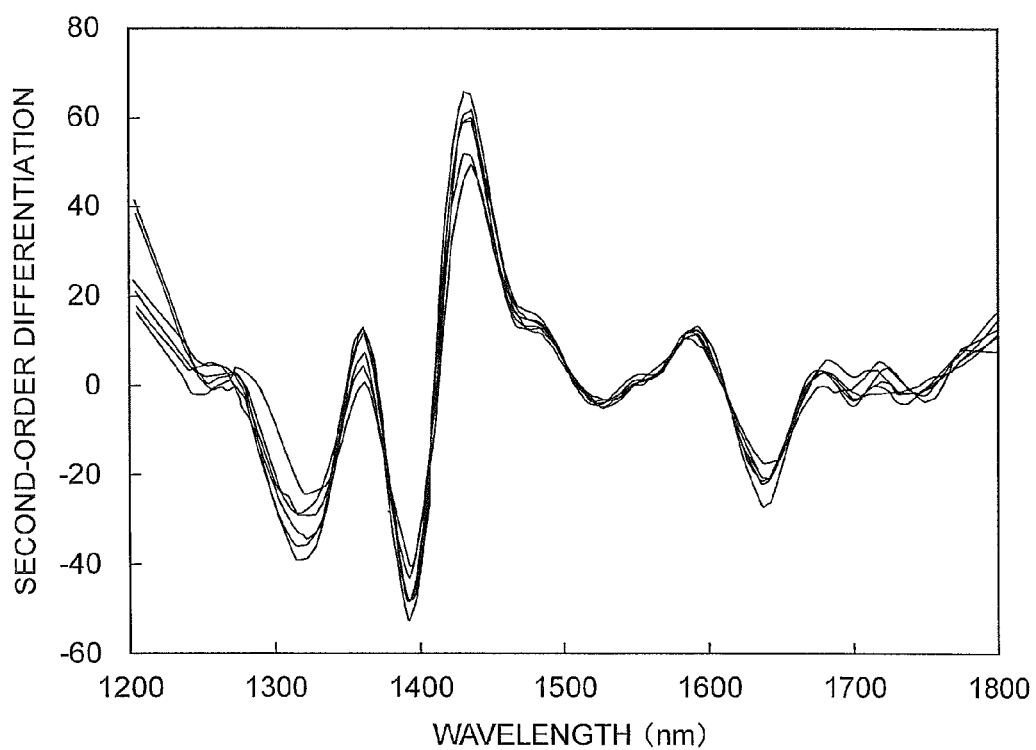
FIG. 12 is a diagram illustrating a result of a second-order differentiation of reflection spectrum information of a third population.
Figure 13:
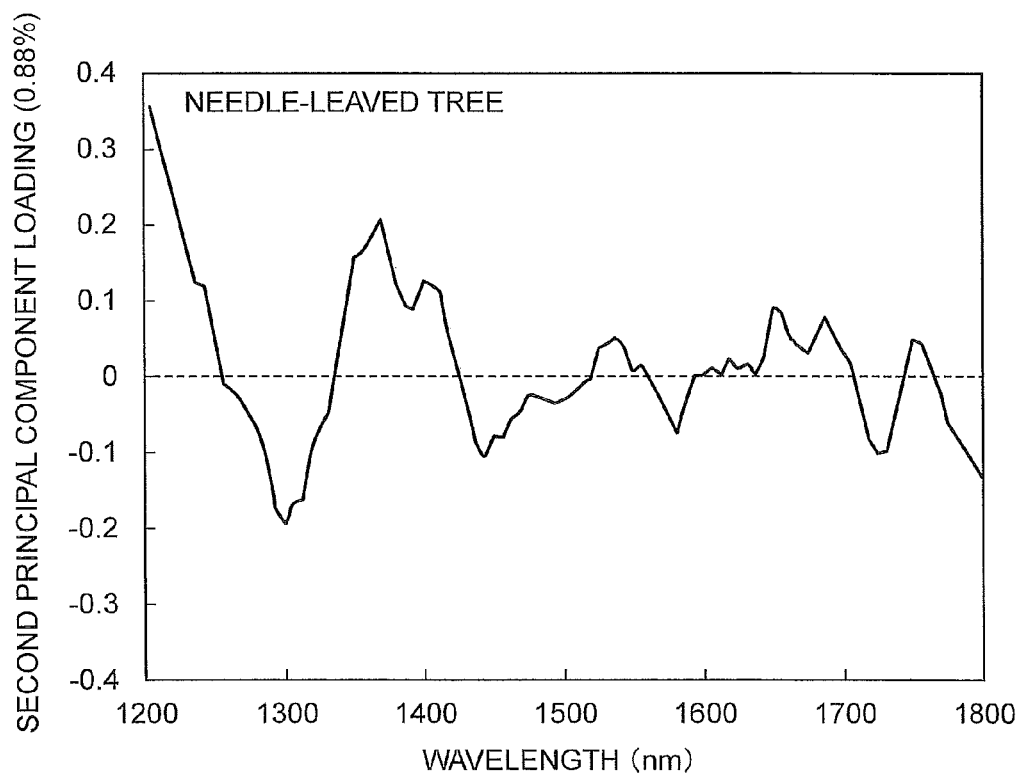
FIG. 13 is a diagram illustrating a third second principal component loading
Figure 14:
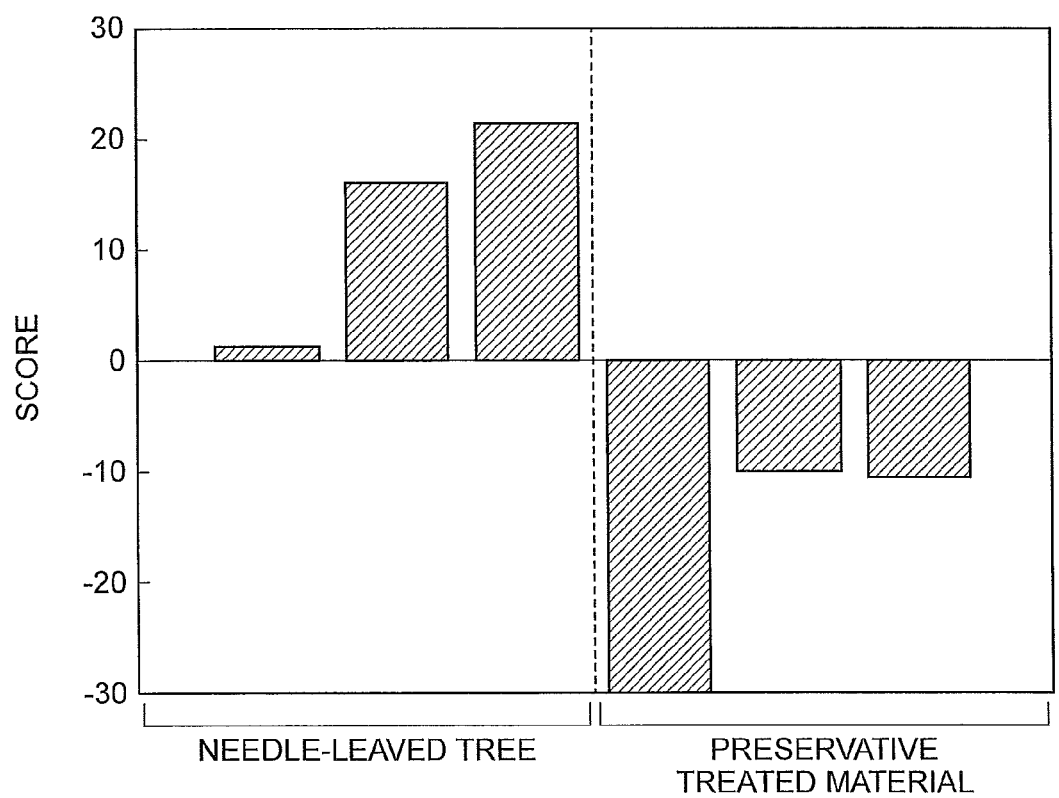
FIG. 14 is a diagram illustrating a result of calculation of scores for the third second principal component loading.

Next, 6 samples which constitute a third population remaining after removing the 3 samples classified into the second group from the second population are used for classification of a third group. First, results of second-order differential processing of the 6 samples of the third population are shown in FIG. 12. Further, a third second principal component loading of a needle-leaved tree acquired by performing a third principal component analysis on the third population is shown in FIG. 13. Further, scores of the 6 samples calculated using a third second principal component loading are shown in FIG. 14. As a result, it was noted that only 3 samples of the needle-leaved tree had higher scores than those of the samples of the other wooden material (a preservative treated material). Therefore, the 3 samples of the needle-leaved tree can be classified into a third group by setting a threshold to, for example −5, and classifying samples satisfying a condition that score >−5 into the third group. Further, a preservative treated member which is not classified in any group among the first to third groups can be classified into a fourth group.

As noted from the above description, an exact classification of even similar materials can be achieved by classifying a specific type of material based on a score of each sample calculated using a second principal component loading obtained as a result of a principal component analysis, removing a classified material from a population, and then performing a principal component analysis again. Further, an unclear kind of wooden material can be clarified through repetition of a step of comparison between a score and a threshold by storing the threshold in the classification and a second principal component loading in each principal component analysis.

According to a method of classifying and discerning wooden materials according to the present embodiment, scores of multiple pieces of reflection spectrum information included in a population are calculated using a first second principal component loading acquired by a principal component analysis, and a first group is then classified based on the calculated scores. Then, scores of multiple pieces of reflection spectrum information included in a population are calculated using a second second principal component loading acquired by a principal component analysis of a second population in which reflection spectrum information of the first group is not included, and a second group is then classified based on the calculated scores. In this event, by performing a second principal component analysis using a second population obtained by removing reflection spectrum information of the first group from the population, it is possible to accurately classify the second group based on minute characteristics of each kind of material included in the reflection spectrum information and it is possible to achieve a classification with high accuracy. Further, because classification of wooden materials can be performed by acquiring reflection spectrum information of the wooden materials, it is possible to achieve a more efficient classification than the conventional classification.

Further, the first second principal component loading and the second second principal component loading obtained by the classification method as described above can be used for classification to determine which group an unknown wooden material belongs to. Therefore, it is possible to determine a classification of an unknown material by using a single piece of unknown reflection spectrum information. Further, the classification using a score based on a first second principal component loading and a score based on a second second principal component loading can be performed with a high accuracy. Therefore, a group to which a wooden material belongs can be determined more conveniently and with a higher accuracy.

Although embodiments of the present invention have been described above, the present invention is not limited to the embodiments described above and various modifications can be made without departing from the scope of the present invention.

For example, although the above description of the measurement system 100 discusses a case of imaging a hyperspectral image, the same classification as in the present embodiment can be also performed in the case of using a spectrum obtained by using a general spectroscope instead of the hyperspectral image. However, it is possible to achieve a higher accuracy to acquire a hyperspectral image of a wooden material and then use an average spectrum based on the acquired hyperspectral image for classification and determination of an unknown sample as in the embodiments described above.

Further, although the above description of the embodiments discusses a case of using reflection spectrum information acquired in a wavelength range of a near-infrared light, reflection spectrum information acquired in other wavelength ranges may also be used.

REFERENCE SIGNS LIST

100: measurement system, 3: measuring object, 10: irradiation means, 11: halogen lamp, 12: irradiation unit, 13: bundle optical fiber, 20: imaging means, 21: slit, 22: spectroscope, 23: light receiving unit, 30: analysis means.

The invention claimed is:

1. A method of classifying wooden materials, comprising:
acquiring a first second principal component loading by performing a principal component analysis on a population including multiple pieces of reflection spectrum information obtained by measuring a plurality of different wooden materials;
calculating a score of the first second principal component loading for each of the multiple pieces of reflection spectrum information included in the population;
classifying into a first group from the population a wooden material having reflection spectrum information having the score belonging to a predetermined range;
acquiring a second second principal component loading by performing a principal component analysis on a second population obtained by removing the reflection spectrum information belonging to the first group from the population;
calculating a second score of the second second principal component loading for each of multiple pieces of reflection spectrum information included in the second population; and
classifying into a second group from the second population a wooden material having reflection spectrum information, the second score of which belongs to a predetermined range.

2. A method of discerning wooden materials comprising:
calculating a first unknown score of the unknown reflection spectrum information by using a first second principal component loading obtained by performing a principal component analysis on a population including multiple pieces of reflection spectrum information obtained by measuring a plurality of different wooden materials, the an unknown reflection spectrum information obtained by measuring an unknown wooden material;
discerning that a wooden material having the unknown reflection spectrum information belongs to a first group when the first unknown score is included in a range of scores of the first second principal component loading, the scores classifying the different wooden materials into the first group from the population;
calculating, when the wooden material having the unknown reflection spectrum information is discerned that it does not belong to the first group, a score of the first second principal component loading for each of the multiple pieces of reflection spectrum information included in the population, classifying into a first group from the population a wooden material having the score of which is included in a predetermined range, and then calculating a second unknown score of the unknown reflection spectrum information by using a second second principal component loading obtained by performing a principal component analysis on a second population obtained by removing the reflection spectrum information belonging to the first group from the population; and
discerning that a wooden material having the unknown reflection spectrum information belongs to a second group when the second unknown score is included in a range of scores of the second second principal component loading, the scores classifying the different wooden materials into the second group from the second population.

* * * * *